(12) United States Patent
Roberts et al.

(10) Patent No.: US 9,586,011 B2
(45) Date of Patent: Mar. 7, 2017

(54) SAFETY DEVICE FOR A PRE-FILLED SYRINGE AND INJECTION DEVICE

(75) Inventors: Gareth Roberts, Wrexham (GB); Sioned Owen, Denbigh (GB); Matthew Ekman, Macclesfiled (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 1058 days.

(21) Appl. No.: 13/808,070

(22) PCT Filed: Jun. 21, 2011

(86) PCT No.: PCT/EP2011/060318
§ 371 (c)(1),
(2), (4) Date: May 15, 2013

(87) PCT Pub. No.: WO2012/000834
PCT Pub. Date: Jan. 5, 2012

(65) Prior Publication Data
US 2014/0303564 A1    Oct. 9, 2014

(30) Foreign Application Priority Data
Jul. 2, 2010    (EP) .................................... 10168316

(51) Int. Cl.
*A61M 5/32*    (2006.01)
*A61M 5/28*    (2006.01)

(52) U.S. Cl.
CPC .......... *A61M 5/3271* (2013.01); *A61M 5/326* (2013.01); *A61M 5/3272* (2013.01);
(Continued)

(58) Field of Classification Search
CPC ...... A61M 5/28; A61M 5/3213; A61M 5/326; A61M 5/3271; A61M 5/3272; A61M 5/3287; A61M 2005/3267
See application file for complete search history.

(56) References Cited

U.S. PATENT DOCUMENTS

2005/0096595 A1*    5/2005    Restelli ................. A61M 5/326
                                                                    604/198
2009/0259178 A1*    10/2009    Brechbuehler ....... A61M 5/326
                                                                    604/110

FOREIGN PATENT DOCUMENTS

EP    1334740 A1    8/2003
FR    2860162 A1    4/2005
(Continued)

OTHER PUBLICATIONS

Form PCT/IPEA/416, Notification of Transmittal of the International Preliminary Report on Patentability.

*Primary Examiner* — Bhisma Mehta
*Assistant Examiner* — Larry R Wilson
(74) *Attorney, Agent, or Firm* — Fish & Richardson P.C.

(57) ABSTRACT

A safety device for a pre-filled syringe comprises a hollow support body to retain the pre-filled syringe therein, a hollow needle shield that is slidable relative to the support body and guiding means for guiding the movement of the needle shield relative to the support body. The guiding means comprise a deflectable flexible arm, a guide pin and a guide track. The deflectable flexible arm extends essentially parallel to a central axis of the safety device. The guide pin extends radial from the flexible arm. The guide track guides the guide pin within and along the guide track when the needle shield is slid relative to the support body.

20 Claims, 10 Drawing Sheets

(52) U.S. Cl.
CPC ............ *A61M 5/28* (2013.01); *A61M 5/3213* (2013.01); *A61M 5/3287* (2013.01); *A61M 2005/3267* (2013.01)

(56) References Cited

FOREIGN PATENT DOCUMENTS

| | | | | | |
|---|---|---|---|---|---|
| FR | 2884722 | A1 | 10/2006 | | |
| FR | 2884723 | A1 | 10/2006 | | |
| FR | WO 2006111860 | A1 | * 10/2006 | ............ | A61M 5/326 |
| WO | 2008025179 | A1 | 3/2008 | | |

* cited by examiner

SAFETY DEVICE FOR A PRE-FILLED SYRINGE AND INJECTION DEVICE

CROSS REFERENCE TO RELATED APPLICATIONS

The present application is a U.S. National Phase Application pursuant to 35 U.S.C. §371 of International Application No. PCT/EP2011/060318 filed Jun. 21, 2011, which claims priority to European Patent Application No. 10168316.7 filed Jul. 2, 2010. The entire disclosure contents of these applications are herewith incorporated by reference into the present application.

TECHNICAL FIELD OF INVENTION

The present invention relates to safety devices that provide needle safety and more particularly to safety devices for pre-filled syringes. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a safety device and a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle. However, there is a need for safety devices comprising a low number of components.

SUMMARY

It is an object of the present invention to provide an improved safety device for a pre-filled syringe.

It is a further object of the invention to provide an improved injection device comprising a pre-filled syringe that is safe to handle and in particular prevents accidental needle pricks.

The object is achieved by a safety device according to claim 1 and by an injection device according to claim 18.

Preferred embodiments are subject of the dependent claims.

In the context of this invention, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, a safety device for a pre-filled syringe comprises a hollow support body to retain the pre-filled syringe therein, a hollow needle shield that is slidable relative to the support body and guiding means for guiding the movement of the needle shield relative to the support body. The guiding means comprise a deflectable flexible arm, a guide pin and a guide track. The deflectable flexible arm extends essentially parallel to a central axis of the safety device. The guide pin extends radially from the flexible arm. The guide track guides the guide pin within and along the guide track when the needle shield is slid relative to the support body.

The guide pin is moved within and along the guide track when the needle shield is slid relative to the support body to cover and/or to expose in particular a hypodermic needle of a pre-filled syringe inserted into the support body of the safety device. As the flexible arm is deflectable in a lateral direction, a relative rotation of any external parts like the needle shield and the support body is unnecessary to guide the guide pin along the guide track. Especially when external parts of the safety device abut the skin of a patient during the injection, friction between these rotating external parts and the skin of the patient is uncomfortable and may even cause pain to the patient, in particular while the hypodermic needle still penetrates the skin. The safety device thus allows for a safe and convenient injection of a medication.

The guiding means of the safety device comprise a longitudinal tongue that is received in a longitudinal groove when the needle shield is moved with respect to the support body in a distal direction, whereby a relative rotation of the needle shield and the support body is prevented. This anti-rotational guiding means ensures the proper interaction of the guide pin with the guide track when the needle shield and the support body is moved axially displaced relative to each other.

The flexible arm is connected to one of the needle shield or the support body. The guide track is formed into the other of the support body or the guide track. Therefore, it is within the scope of the present invention that the safety device comprises a support body with a guide track and a needle shield with a flexible arm, or alternatively, that the flexible arm is connected to the support body and a guide track is formed into the needle shield.

Preferably, the flexible arm is integrally formed to the needle shield or to the support body. The safety device comprises only a small number of parts that are cost-efficiently mass-produced allowing the safety device to be used as a single-use disposable device that provides needle safety for disposable pre-filled syringes.

The flexible arm is deflectable and energizable by the action of a relaxing spring means, e.g. a compression spring, biasing the needle shield in the retracted position. Thus, no additional effort is required from the user performing the injection to energize the flexible arm.

According to a possible embodiment, the guide pin is located in an intermediate position in proximity of a proximal end of the guide track when the needle shield is in a retracted position and in an end position in proximity of a distal end of the guide track when the needle shield is an advanced position.

The needle shield is substantially received in the support body in the retracted position and protrudes the distal end of the support body in the advanced position. The movement of the guide pin within and along the guide track controls the extension and/or retraction of the needle shield allowing for a safe injection.

Alternatively, the substantial cylindrical needle shield comprises a radial diameter that is sized to substantially receive the support body in the retracted position. In this alternative embodiment the support body slides into the needle shield when the needle shield is moved from the advanced to the retracted position.

In a possible embodiment of the invention, the movement of the needle shield is controlled in a way as to hide the hypodermic needle from the view of a user throughout the injection. This reduces the fear of performing in particular self-administered subcutaneous injections that patients suffering from diabetes frequently have to carry out.

The guide pin in the end position is prevented from moving in a proximal direction by an interaction between the guide track and the guide pin, so that the needle shield is locked in the advanced position. The safety device is rendered non-reusable after the first use, whereby a further interaction or attention of the user is not required.

The guide pin in the start position, in the end position and in the intermediate position is non-biased in a lateral direction perpendicular to the central axis. The flexible arm is deflected to bias the guide pin during use of the safety device. The safety device is stored with the guide pin retained in the start position, wherein the flexible arm is not stressed and in an equilibrium position. This avoids material fatigue and associated mechanism failure even after prolonged periods of storage.

The guide pin in the end position is in an equilibrium position locking the needle shield in the advanced position and preventing re-usage of the safety device. As the guide pin is non-biased in the lateral direction in the intermediate position, occurring friction between the guide pin and the guide track is minimized during the injection stroke performed by the user, so that the injection stroke can be carried out with minimal effort.

The flexible arm is deflected to bias the guide pin in the lateral direction when the guide pin moves along the guide track from the intermediate position towards the end position. As the flexible arm is typically made from a resilient plastics material that is prone to fatigue of material, it is advantageous to deflect and energize the flexible arm during use of the safety device, so that the shelf-life of the safety device is extended.

According to a possible embodiment of the invention, the needle shield protrudes the support body in an initial position and the spring mean is in a partially energized state when the needle shield is in the initial position. As the safety device is stored with the needle shield in the initial position, fatigue of material of the spring mean is avoided by only partially energizing the spring mean. This allows for a reliable use of the safety device even after prolonged periods of storage.

According to a possible embodiment, the needle shield is made from an opaque plastics material. The hypodermic needle is hidden from the view of the patient before the injection by the needle shield that is retained in the initial position. This eases a possible fear of needles of the patient. The safety device is thus particularly suited for performing self-administered injections.

According to an alternative embodiment, the needle shield is made from a transparent plastics material. A healthcare professional that uses the safety device thus can visually confirm the correct placement of the hypodermic needle penetrating the skin of the patient, even when the hypodermic needle is surrounded by the needle shield.

As the safety device is both suited for self-administered injections and injections carried out by a healthcare professional, the person referred to as the user or the patient may be one and the same person.

In a possible embodiment of the invention, the needle shield of the safety device is retained in the initial position prior to use by a resilient flexing gate element releasably retaining the guide pin in a start position located between the distal and the proximal end of the guide track. The flexing gate element serves as a simple means to releasably retain the needle shield connected to the guide pin in the initial position, whereas the needle shield protrudes the distal end of the support body to surround the hypodermic needle of the pre-filled syringe before the injection.

According to the same embodiment of the invention, the resilient flexing gate element guides the movement of the guide pin within the guide track, so that the movement of the needle shield relative to the support body is controlled in a manner that avoids a relative rotation of needle shield and support body.

According to the same embodiment, the flexing gate element is deflectable in a lateral direction as to allow the guide pin to move proximally from the start to the intermediate position. In particular, the flexing gate element is integrally formed into the support body and establishes a section of narrowed width that the guide pin has to pass to leave the start position and to activate the needle safety features of the safety device. A user typically applies a force to the needle shield in a distal direction to activate the safety features, so that the guide pin passes the section of narrowed width, whereby the flexing gate element is laterally deflected. Thus, an inadvertent activation of the needle safety features is prevented by the flexing gate element that retains the guide pin in the start position in particular during transportation of the safety device prior to use.

The flexing gate element of the same embodiment comprises a sloped section that guides the movement of the guide pin along a section of the guide track from the intermediate to the end position and prevents the guide pin from re-entering the start position. The safety device is non-reusable after a single injection has been performed and thus adapted to be used in combination with a disposable pre-filled syringe.

According to another embodiment of the invention, the needle shield further comprises at least one radial outwardly protruding retaining catch that can be engaged by a release flap formed into the support body. The needle shield is releasably retained within the support body by the release flap and the retaining catch in the retracted position. The release flap is hinged to the support body. The release flap is engaged by an interior surface of the outer body at the end of an injection stroke, whereas the release flap presses the retaining catch inwards to release the needle shield. This mechanism prevents an unintended early release of the needle shield and makes sure that the medication has been fully delivered before the needle shield is released.

In yet another embodiment of the invention, the outer body comprises an inward projection that abuts the guide pin in the intermediate position to retain the needle shield in the retracted position. This simple mechanism allows for a secure retention of the needle shield in the retracted position.

According to the same embodiment, the guide pin and the inward projection comprise a triangular cross-section, so that upon releasing the needle shield from being retained in the retracted position, the guide pin is redirected in the lateral direction and guided within and along the guide track. This minimizes friction between the guide pin, the guide track and the inward projection allowing for a smooth use of the safety device.

The inward projection of the same embodiment moves along a section of the guide track thereby releasing the needle shield from being retained in the retracted position. The mechanism for both retaining and releasing the needle shield is integrated in existing parts having additional functionality. The safety device has a low part count that can be cost-efficiently produced.

An injection device comprises a pre-filled syringe retained in the support body of the safety device. The pre-filled syringe comprises a hypodermic needle attached to a distal end of the pre-filled syringe, a barrel with an inner cavity in fluid communication with the hypodermic needle and a piston fluid-tightly sealing a proximal end of the inner cavity. The piston is movable by actuating a piston rod protruding a proximal end of the barrel. The pre-filled syringe is retained within the support body of the safety device, so that the hypodermic needle protrudes the distal end of the support body. The hypodermic needle of the injection device is surrounded by the needle shield in the initial position and/or in the advanced position and the hypodermic needle is exposed when the needle shield is in the retracted position. The injection device comprising the pre-filled syringe and the safety device combines the aforementioned advantages and avoids inadvertent needle sticks before, during and after an injection delivering the medication beneath the skin of patient.

The injection device is particularly suited for self-administered subcutaneous and intramuscular injections.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
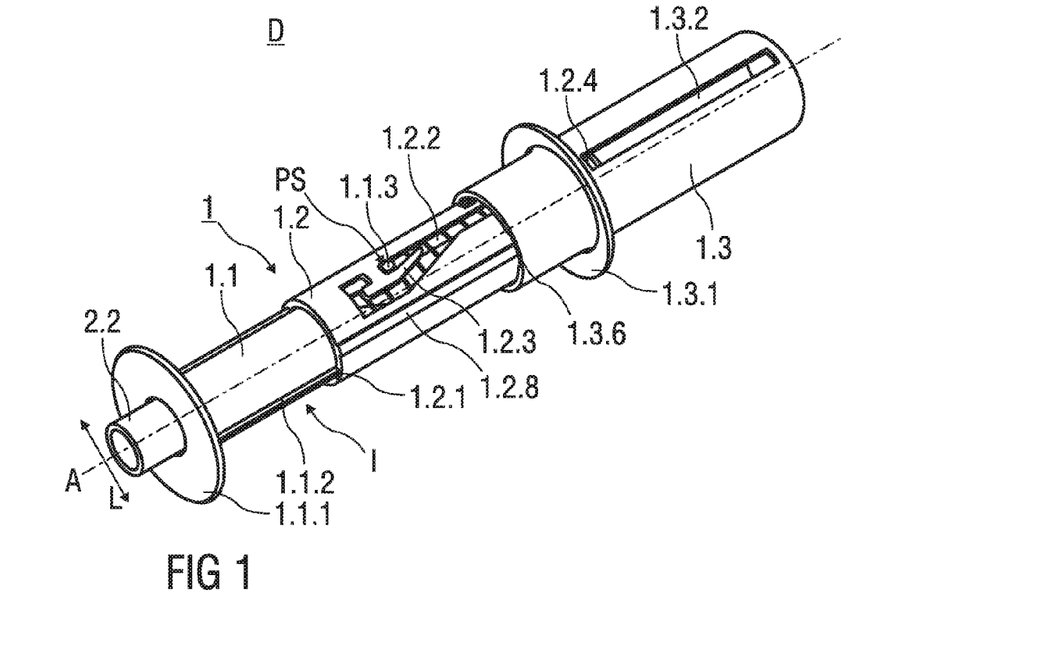
FIG. 1 shows a perspective view of an injection device with a safety device and a pre-filled syringe according to a first embodiment of the invention.

FIG. 1 shows an injection device D comprising a safety device 1 and a pre-filled syringe 2. The injection device D is in a packaged state as it would be presented to a user performing an injection. The safety device 1 comprises a substantially cylindrical and hollow needle shield 1.1. The needle shield 1.1 is received within a substantially cylindrical and hollow support body 1.2, whereas the needle shield 1.1 is slidable with respect to the support body 1.2. Prior use of the safety device 1, the needle shield 1.1 is retained in an initial position I, wherein the needle shield 1.1 protrudes the support body 1.2.

The needle shield 1.1 further comprises a circumferential skin-contact flange 1.1.1 at its distal end. The skin-contact flange 1.1.1 is adapted to be pressed against the skin of a patient and protrudes radial outwardly and perpendicular to a central axis A.

The injection device D comprises the safety device 1 with the pre-filled syringe 2 retained within the support body 1.2. In the packaged state as shown in FIG. 1, a hypodermic needle 2.1 is covered by a needle cap 2.2 preferably at least partially made from a plastics material like rubber. The needle cap 2.2 protrudes the skin-contact flange 1.1.1 of the safety device 1 in a distal direction, so that the user can easily remove the needle cap 2.2 from the pre-filled syringe 2.

Two diametrical opposing longitudinal tongues 1.1.2 are formed to an exterior surface of the needle shield 1.1 that protrude radial outwardly. Each longitudinal tongue 1.1.2 extends over an axial length parallel to the central axis A of the substantially cylindrical needle shield 1.1. The longitudinal tongue 1.1.2 is received in a corresponding longitudinal groove 1.2.1 formed into an interior surface of the support body 1.2 to prevent a rotation of the needle shield 1.1 relative to the support body 1.2.

Additionally, a longitudinal notch 1.2.8 is formed into an outer surface of the support body 1.2. An outer body 1.3 is slidably arranged relative to the support body 1.2. An inwardly protruding dent is formed into an inner surface of the substantially hollow outer body 1.3 that is received in the longitudinal notch 1.2.8. The outer body 1.3 is moved relative to the support body 1.2. This prevents a rotation of the outer body 1.3 relative to the support body 1.2, so that in particular the outer body 1.3 can be slid with respect to the support body 1.2 in the distal direction to perform a linear injection stroke.

Figure 2:
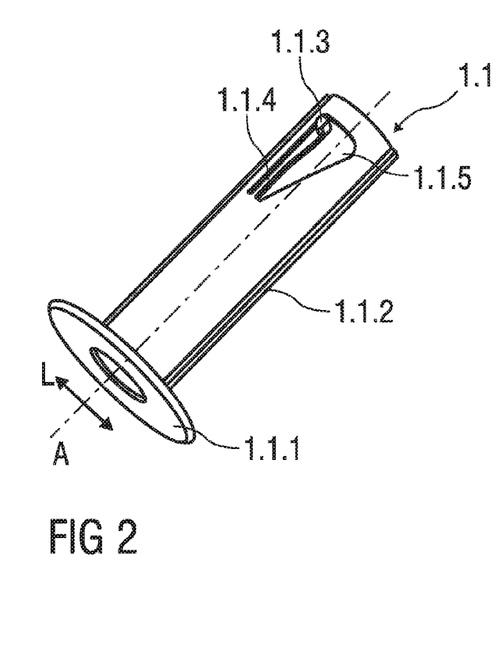
FIG. 2 shows a perspective view of a needle shield with a laterally deflectable flexible arm.

As best seen in FIG. 2, a guide pin 1.1.3 is integrally formed to a flexible arm 1.1.4 of the needle shield 1.1. As illustrated in FIG. 1, the guide pin 1.1.3 protrudes radial outwardly into a guide track 1.2.2 formed into the substantially cylindrical support body 1.2. Prior to use of the safety device 1, the guide pin 1.1.3 is retained within the guide track 1.2.2 in a start position PS located between a proximal end and a distal end of the guide track 1.2.2.

The guide pin 1.1.3 is retained in the start position PS by a flexing gate element 1.2.3 that is deflectable in a lateral direction L perpendicular to the central axis A and is formed to the support body 1.2. The flexing gate element 1.2.3 is curved towards one side to form a narrowed section that the guide pin 1.1.3 has to pass to leave the start position PS. As the guide pin 1.1.3 is integrally connected to the needle shield 1.1, the needle shield 1.1 is retained in the initial position I when the guide pin 1.1.3 is held by the flexing gate element 1.2.3 in the start position PS. The flexing gate element 1.2.3 is laterally deflectable to allow the guide pin 1.1.3 to move within the guide track 1.2.2 in a distal direction.

The safety device 1 comprises the essentially cylindrical and hollow outer body 1.3 with an open distal and a closed proximal end. The proximal end of the support body 1.2 is received within the open distal end of the outer body 1.3, whereas the outer body 1.3 is slidable with respect to the support body 1.2 in a distal direction to substantially receive the support body 1.2 inside the outer body 1.3.

A circumferential and outwardly protruding hand flange 1.3.1 is integrally formed to an exterior surface of the outer body 1.3 close to its distal end.

Two longitudinal recesses 1.3.2 are formed into the outer body 1.3 that extend over a substantial axial length of the outer body 1.3 and parallel to the central axis A.

Each longitudinal recess 1.3.2 receives a corresponding outward projection 1.2.4 integral part of the support body 1.2. The outward projection 1.2.4 moves within the longitudinal recess 1.3.2 when the outer body 1.3 is slid relative to the support body 1.2 to perform the injection stroke, whereas a relative rotation of the outer body 1.3 relative to the support body 1.2 is prevented.

The longitudinal recess 1.3.2 shown in FIG. 1 has the form of a slot. Alternatively, the longitudinal recess 1.3.2 is formed into an inner surface of the outer body 1.3, so that the outward projection 1.2.4 moves along the longitudinal recess 1.3.2 within the outer body 1.3 and is inaccessible from the outside.

Figure 3:
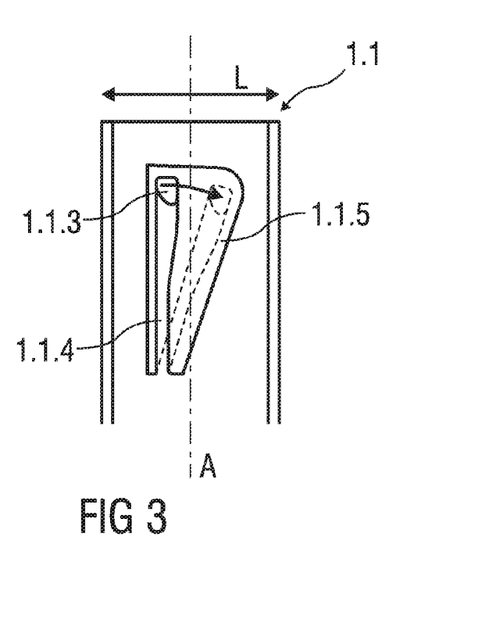
FIG. 3 shows a side view of a needle shield with a laterally deflectable flexible arm.

FIGS. 2 and 3 show details of the essentially tubular needle shield 1.1 comprising the skin-contact flange 1.1.1 and the flexible arm 1.1.4 having the guide pin 1.1.3 formed to its proximal end. The flexible arm 1.1.4 and the guide pin 1.1.3 are integral parts of the needle shield 1.1 that is favourably made from a resilient plastics material.

Preferably, two flexible arms 1.1.4 are formed into opposite sides of the needle shield 1.1, whereas each flexible arm 1.1.4 comprises a guide pin 1.1.3. Correspondingly, two guide tracks 1.2.2 are formed into opposite sides of the support body 1.2, whereas one guide pin 1.1.3 travels within one of the guide tracks 1.2.2.

The flexible arm 1.1.4 extends over a substantial axial length of the needle shield 1.1. A wedge-shaped cut-out 1.1.5 is formed into the needle shield 1.1 to allow for a deflection of the flexible arm 1.1.4 in the lateral direction L. The flexible arm 1.1.4 extends essentially parallel to the central axis A in its equilibrium position and, as indicated in FIG. 3 by a dashed line, is oriented at an acute angle with respect to the central axis A when the flexible arm 1.1.4 is laterally deflected. The flexible arm 1.1.4 in the laterally deflected state is stressed and biased towards its equilibrium position. The guide pin 1.1.3 moves along an arc and on a cylindrical surface of the needle shield 1.1 when the flexible arm 1.1.4 is laterally deflected.

Figure 4:
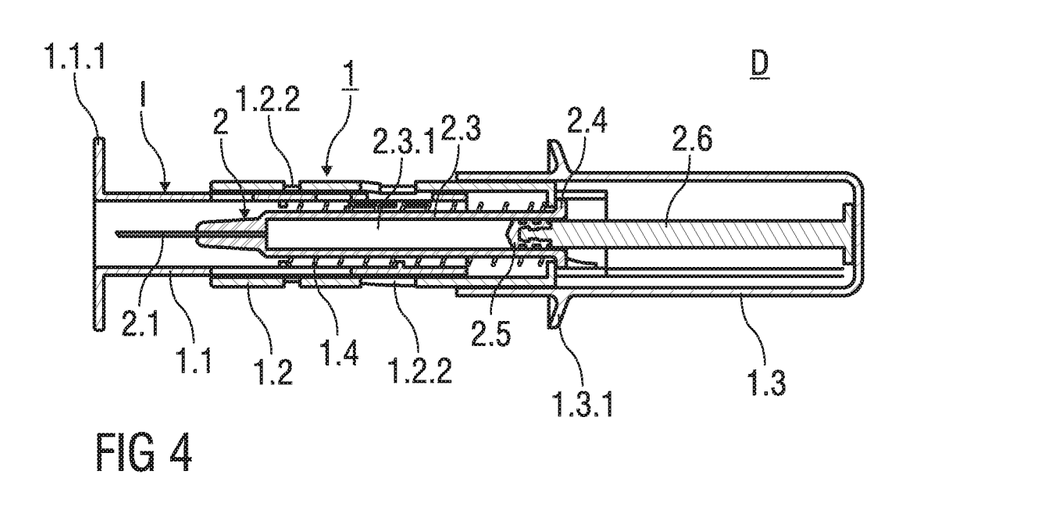
FIG. 4 shows a sectional view of an injection device according to the first embodiment, whereas a needle shield is in an initial position.

FIG. 4 shows a sectional view of the injection device D comprising the safety device 1 and the pre-filled syringe 2 retained within the support body 1.2. The pre-filled syringe 2 has a barrel 2.3 with a collar 2.4 and an inner cavity 2.3.1 that is in fluid communication with the hypodermic needle 2.1. The medication contained in the inner cavity 2.3.1 can be distally expelled through the hollow hypodermic needle 2.1 by a distal movement of a piston 2.5, which provides a liquid-tight seal of a proximal end of the inner cavity 2.3.1. The piston 2.5 is connected to a piston rod 2.6 proximally extending from a barrel 2.3, whereas the piston 2.5 is movable within the inner cavity 2.3.1 by actuating the piston rod 2.6.

A proximal end of the piston rod 2.6 abuts the closed distal end of the outer body 1.3, so that the piston 2.5 is movable in a distal direction by the distal displacement of the outer body 1.3 with respect to the support body 1.2.

Alternatively, the piston rod 2.6 is connected to the outer body 1.3 or an integral part of the outer body 1.3. This alternative embodiment has additional advantage of a low overall part count, so that manufacturing costs are reduced.

The needle shield 1.1 is in the initial position I surrounding the hypodermic needle 2.1 of the pre-filled syringe 2. A spring mean 1.4 is arranged within the safety device 1 in a partially energized state bearing distally against an inner surface of the needle shield 1.1 and proximally against an inner surface of the support body 1.2, thereby biasing the two parts 1.1, 1.2 away from each other. The spring mean 1.4 may be provided as a compression spring, a tension spring or a torsion spring. The needle shield 1.1 is retained in the initial position I by the guide pin 1.1.3 abutting against the support body 1.2 in the start position PS.

Figure 5:
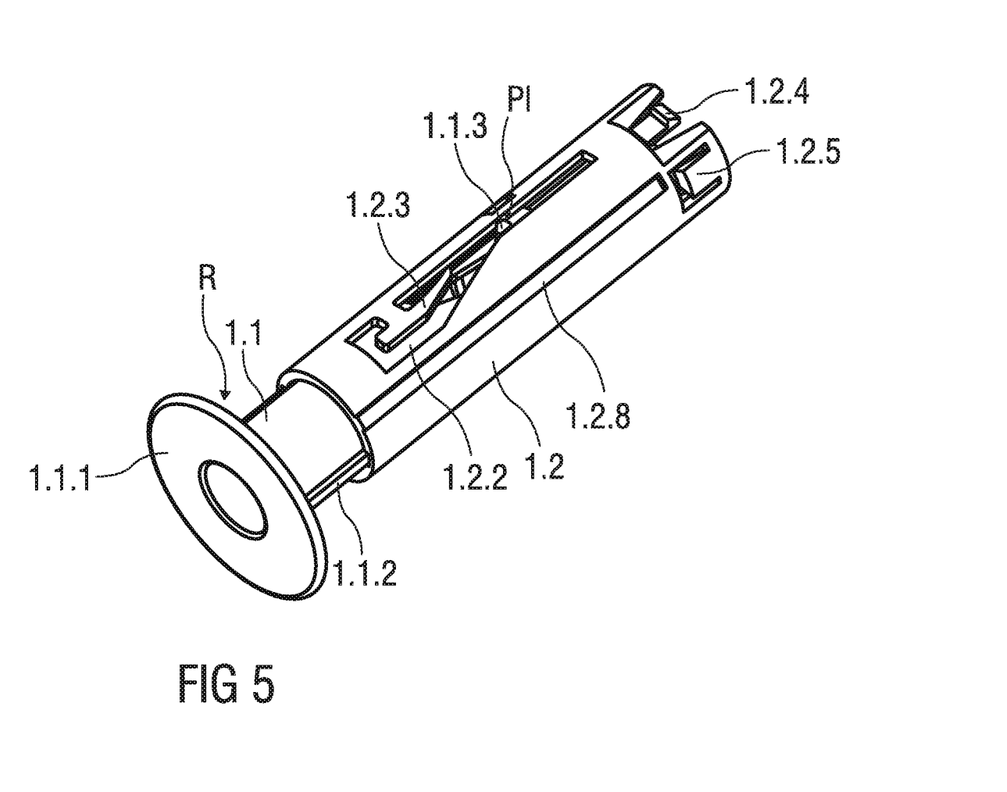
FIG. 5 shows a perspective view of a needle shield that is retracted within a support body according to the first embodiment of the invention.

FIG. 5 shows a perspective view of the needle shield 1.1 in a retracted position R that is substantially received within the support body 1.2. The guide pin 1.1.3, that is integral part of the needle shield 1.1 is in an intermediate position PI within the guide track 1.2.2 and in proximity of a proximal end thereof. The intermediate position PI corresponds to the retracted position R of the needle shield 1.1.

The support body 1.2 further comprises two clips 1.2.5 arranged diametrical opposite to each other. The clips 1.2.5 are located near the proximal end of the support body 1.2 and clamp to the collar 2.4 of the pre-filled syringe 2 to affix the pre-filled syringe 2 to the support body 1.2, so that the pre-filled syringe 2 is firmly retained within the support body 1.2.

Figure 6:
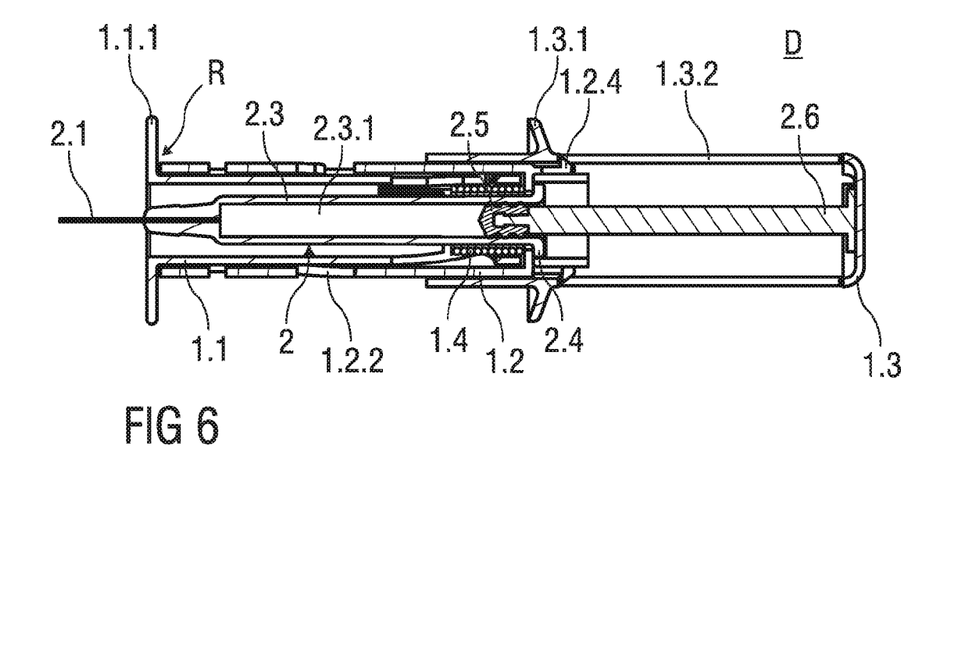
FIG. 6 shows a sectional view of an injection device according to the first embodiment, whereas a needle shield is in a retracted position.

FIG. 6 shows a sectional view of the injection device D. The needle shield 1.1 is in the retracted position R, so that the hypodermic needle 2.1 distally protrudes the skin-contact flange 1.1.1 of the needle shield 1.1. The spring mean

1.4 that is arranged within the safety device 1 between the needle shield 1.1 and the support body 1.2 is compressed and thus fully energized.

Figure 7:
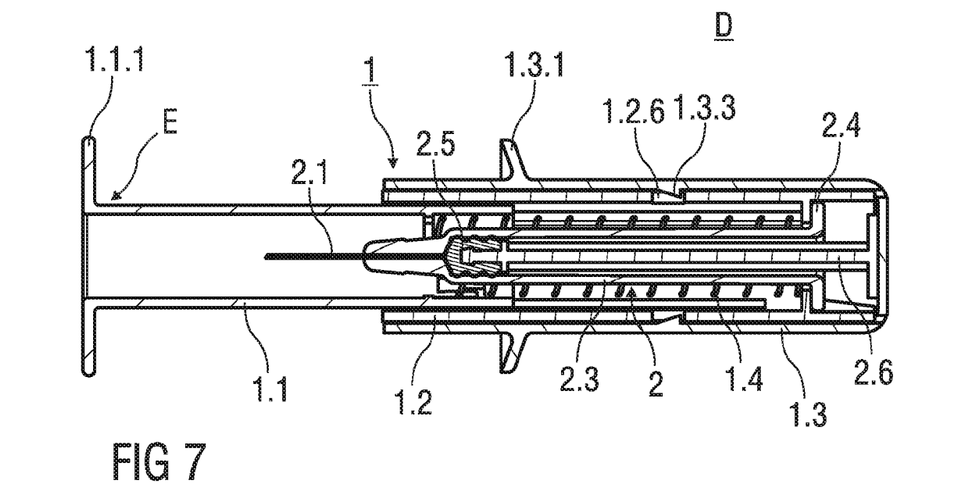
FIG. 7 shows a sectional view of an injection device according to the first embodiment, whereas a needle shield is in an advanced position and a support body is received in an outer body.

FIG. 7 shows a sectional view of the injection device D according to the first embodiment after the injection of the medication. The sectional view given in FIG. 7 is rotated with respect to the sectional views shown in FIGS. 4 and 6 about an angle of 90 degrees around the central axis A. The needle shield 1.1 is in an advanced position E distally protruding from the support body 1.2, whereas the hypodermic needle 2.1 is surrounded by the needle shield 1.1 to avoid needle pricks. The needle shield 1.1 is fixed to the advanced position E by the guide pin 1.1.3 being retained in an end position PE in proximity of a distal end of the guide track 1.2.2.

The piston 2.5 is fully depressed inside the barrel 2.3 of the pre-filled syringe 2. The support body 1.2 is received within the outer body 1.3 and locked to it, so that a re-usage of the safety device 1 is prevented. An inwardly protruding locking catch 1.3.3 is formed to an inner surface of the outer body 1.3 that engages a corresponding locking recess 1.2.6 formed into the support body 1.2 to irreversibly lock the support body 1.2 with respect to the outer body 1.3.

FIG. 8A to 8D show in detail the form of the guide track 1.2.2 according to the first embodiment of the invention and the movement of the guide pin 1.1.3 within and along the guide track 1.2.2 during an injection.

Figures 8A, 8B, 8C, 8D:
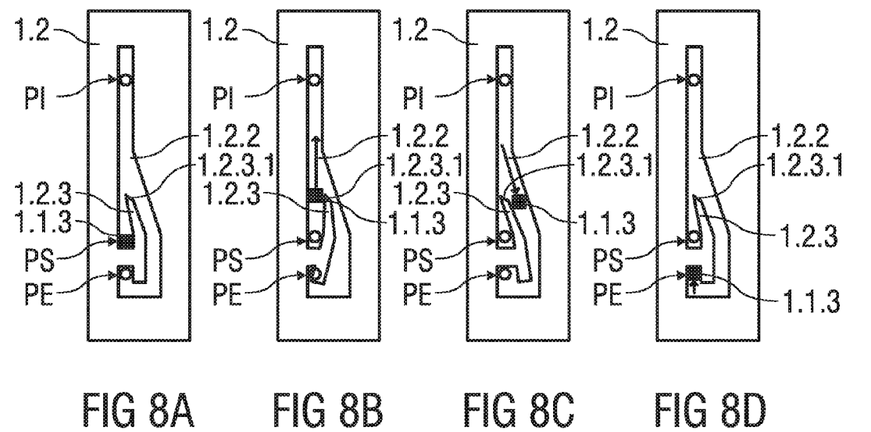
FIGS. 8A to 8D show a guide track formed into a support body and the movement of a guide pin within and along the guide track during an injection according to the first embodiment.

Prior to the injection, the guide pin 1.1.3 is retained by the flexing gate element 1.2.3 in the start position PS, as shown in FIG. 8A, affixing the needle shield 1.1 to the initial position I. In the initial position I, the hypodermic needle 2.1 is surrounded by the needle shield 1.1.

The needle shield 1.1 is made from an opaque plastics material, so that the hypodermic needle 2.1 is hidden from view of the patient throughout the injection.

Alternatively, the needle shield 1.1 is made from a transparent plastics material, so that a healthcare professional performing the injection may visually confirm the correct placement of the hypodermic needle 2.1 before penetrating the skin of the patient.

The injection is carried out by orientating the central axis A essentially perpendicular to the skin of the patient, whereas the skin-contact flange 1.1.1 of the needle shield 1.1 rests on the skin surface of the patient and the proximal section of the outer body 1.3 proximal of the hand flange 1.3.1 is gripped by the user performing the injection. The hand flange 1.3.1 supports the hand of the user to carry out an injection stroke.

The injection is carried out in stages. In a first stage, the needle shield 1.1 is pushed inside the support body 1.2 in the proximal direction against the biasing force of the spring mean 1.4. The guide pin 1.1.3 leaves its start position PS, whereby the flexing gate element 1.2.3, as indicated by FIG. 8B, is laterally deflected. The guide pin 1.1.3 passes the section of narrowed width and moves proximally along the guide track 1.2.2 until it reaches the intermediate position PI.

Figure 9:
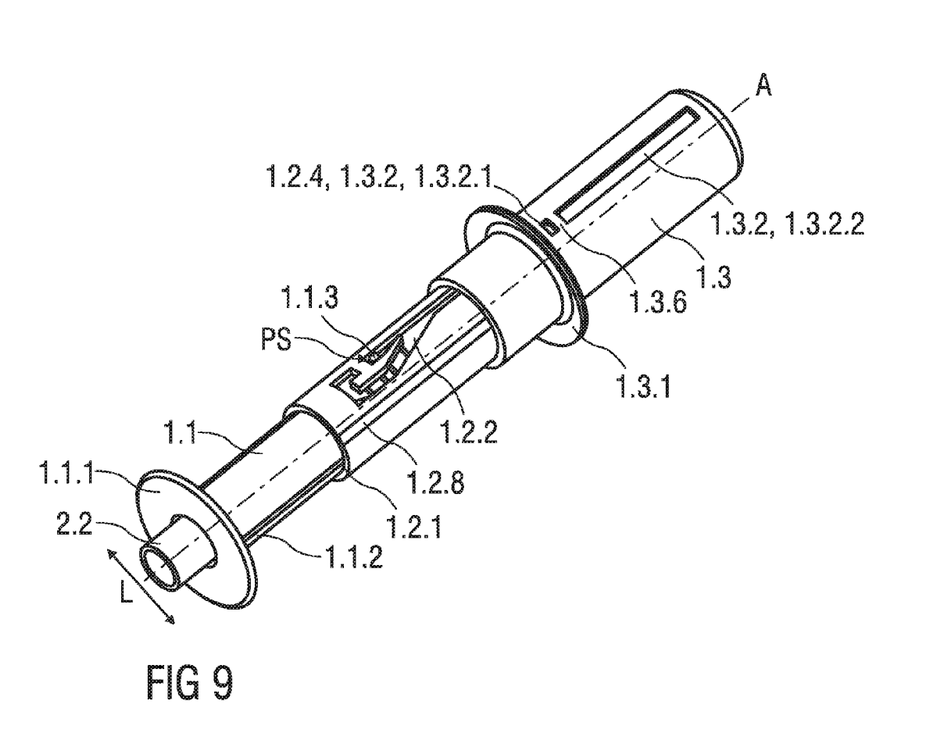
FIG. 9 shows a perspective view of an injection device according to an alternative first embodiment of the invention.

FIG. 9 shows an alternative embodiment of the safety device 1. The longitudinal recess 1.3.2 is separated by a web 1.3.6 in a distal section 1.3.2.1 and a proximal section 1.3.2.2. During the first stage of the injection, the outward projection 1.2.4 is retained in the distal section 1.3.2.1 of the longitudinal recess 1.3.2 to block a relative movement of the outer body 1.3 relative to the support body 1.2 until the needle shield 1.1 reaches the retracted position R and the guide pin the intermediate position PI.

As soon as the guide pin 1.1.3 passes the section of narrowed width as shown in FIG. 8B, the needle safety features, that in particular prevent re-usage of the injection device D and the safety device 1, are activated.

When the guide pin 1.1.3 is in the intermediate position PI, the needle shield 1.1 is in the retracted position R, so that the hypodermic needle 2.1 protrudes the skin-contact flange 1.1.1 and penetrates the skin of the patient. The hypodermic needle 2.1 protrudes the skin-contact flange 1.1.1 by a length that corresponds to a penetration depth of the hypodermic needle 2.1. The spring mean 1.4 is fully energized when the needle shield 1.1 is in the retracted position R.

In the alternative embodiment of FIG. 9, the continued force exerted upon the outer body 1.3 in the distal direction after the pre-defined penetration depth of the hypodermic needle 2.1 has been reached, causes the outward projection 1.2.4 to pass the web 1.3.6. The outward projection 1.2.4 protrudes into the proximal section 1.3.2.2 of the longitudinal recess 1.3.2 in the following second stage of the injection. As the proximal section 1.3.2.2 of the longitudinal recess 1.3.2 extends over a substantial length of the outer body 1.3, the outer body 1.3 becomes slidable with respect to the support body 1.2.

In the second stage, the outer body 1.3 moves with respect to the support body 1.2 in the distal direction. Simultaneously, the piston rod 2.6 interacting with the outer body 1.3 is actuated to move the piston 2.5 in the distal direction, whereby the medication contained in the inner cavity 2.3.1 is delivered through the hypodermic needle 2.1 and beneath the skin of the patient.

At the end of the injection stroke, the support body 1.2 is substantially received within the outer body 1.3. The locking catch 1.3.3 engages the locking recess 1.2.6 to permanently lock the support body 1.2 to the outer body 1.3.

The injection device D comprising the safety device 1 with the pre-filled syringe 2 received therein is taken away from the skin surface. The needle shield 1.1 immediately moves distally by the action of the relaxing spring mean 1.4 thereby re-sheathing the hypodermic needle 2.1. The guide pin 1.1.3 moves with the needle shield 1.1 distally, whereby it abuts a sloped section 1.2.3.1 of the flexing gate element 1.2.3 that is curved towards one side of the guide track 1.2.2, as illustrated in FIG. 8C. The flexing gate element 1.2.3 is laterally deflected towards said side of the guide track 1.2.2 preventing the guide pin 1.1.3 to re-enter the start position PS. The guide pin 1.1.3 is redirected by the sloped section 1.2.3.1 of the flexing gate element 1.2.3 in a lateral direction opposite to said side of the guide track 1.2.2, so that the guide pin 1.1.3 moves further distally towards the end position PE.

As the guide pin 1.1.3 travels in the distal and in the lateral direction, the flexible arm 1.1.4 is deflected laterally thereby biasing the guide pin 1.1.3 in the lateral direction towards the end position PE.

When the guide pin 1.1.3 reaches the distal most portion of the guide track 1.2.2 the guide pin 1.1.3 is moved by the action of the relaxing flexible arm 1.1.4 until it reaches the end position PE, as shown in FIG. 8D.

The guide pin 1.1.3 is securely retained in the end position PE and abuts the support body 1.2 in a proximal direction thereby preventing a subsequent proximal movement of the needle shield 1.1 relative to the support body 1.2. A lateral deflection of the guide pin 1.1.3 is prevented by the form of the guide track 1.2.2 at the end position PE and by the flexible arm 1.1.4.

The needle shield 1.1 is firmly retained in the advanced position E by the guide pin 1.1.3 being retained in the end position PE, whereby a re-usage of the injection device D and/or the safety device 1 is prevented.

In a possible embodiment of the invention, the hypodermic needle 2.1 is hidden from the view of the patient throughout the injection.

The injection is carried out and the needle safety features of the safety device 1 are activated by a single linear movement of outer body 1.3 towards the skin of the patient.

Figure 10:
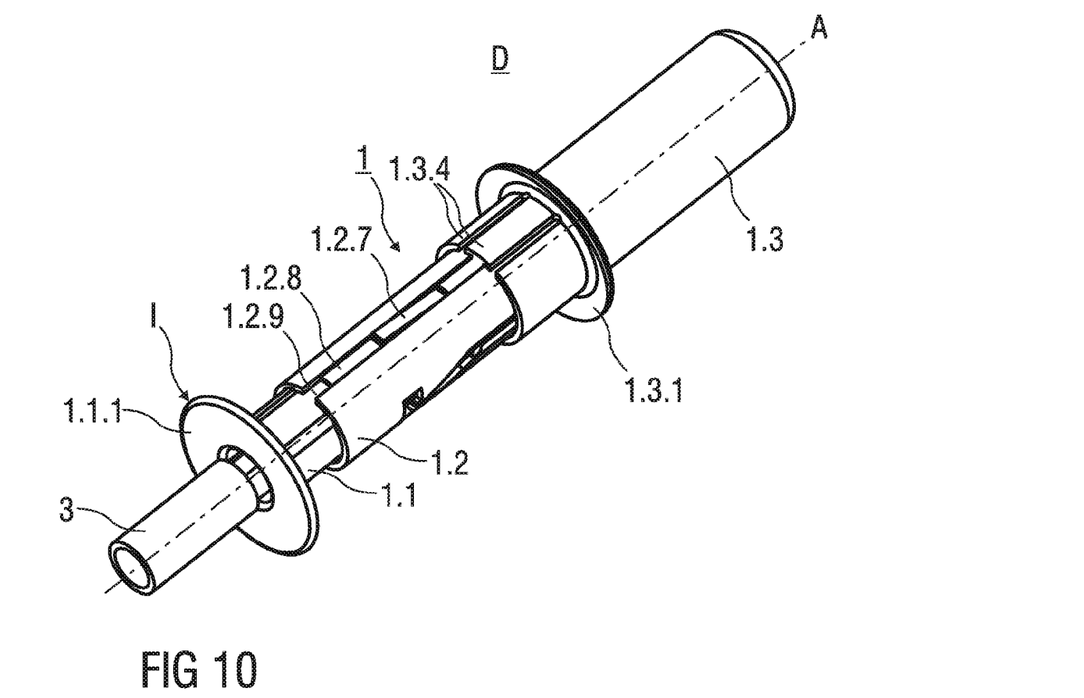
FIG. 10 shows a perspective view of an injection device according to a second embodiment of the invention.

FIG. 10 shows a perspective view of the injection device D according to a second embodiment of the invention. The support body 1.2 of the safety device 1 comprises at least one release flap 1.2.7 hinged to the support body 1.2. The release flap 1.2.7 protrudes outwards at an acute angle relative to the central axis A and is located in a longitudinal notch 1.2.8 formed into an outer surface of the support body 1.2, whereas the longitudinal notch 1.2.8 extends over a substantial axial length of the support body 1.2.

At least one inwardly protruding dent 1.3.4 is formed to an interior surface of the outer body 1.3 that is sized to move within and along the longitudinal notch 1.2.8 and over the release flap 1.2.7 when the outer body 1.3 is slid relative to the support body 1.2.

Preferably, two longitudinal notches 1.2.8 and two release flaps 1.2.7 are formed into opposite sides of the support body 1.2.

A cylindrical needle cap remover 3 is detachably attached to a distal end of the needle cap 2.2 frictionally held on a distal end of the pre-filled syringe 2 to facilitate removal of the needle cap 2.2 when the pre-filled syringe 2 is assembled within the safety device 1. The needle cap remover 3 has a proximal end that snugly fits over and frictionally engages the distal end of the needle cap 2.2, so that the needle cap 2.2 can be pulled off the pre-filled syringe 2 arranged inside the safety device 1 by a distal movement of the needle cap remover 3. The cylindrical needle cap remover 3 has an outer diameter that allows the needle cap remover 3 to be inserted into the distal end of the needle shield 1.1, so that the needle cap 2.2 can be easily pulled off the pre-filled syringe 2 even when the distal end of the needle cap 2.2 is surrounded by the needle shield 1.1.

Figure 11:
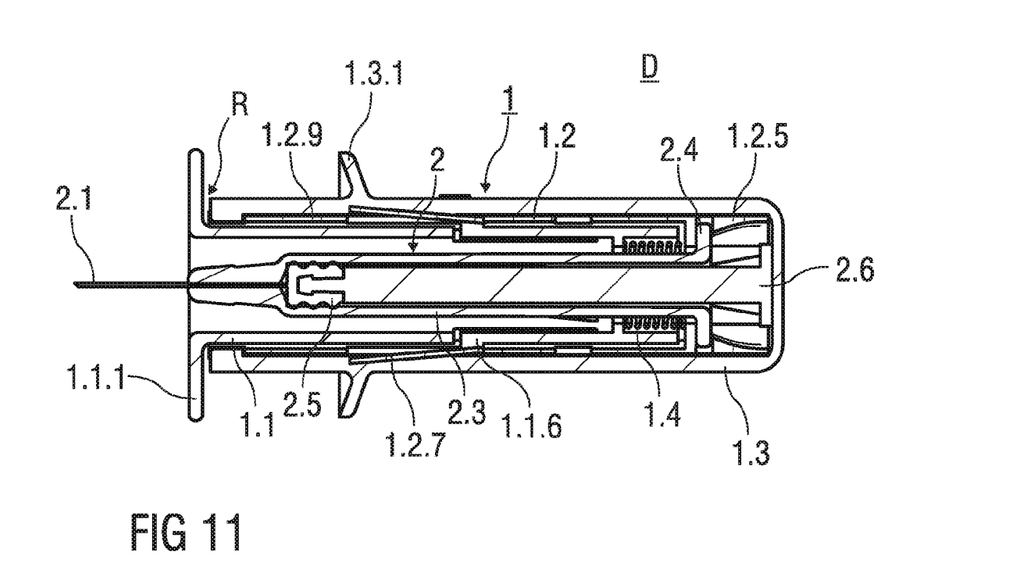
FIG. 11 shows a sectional view of an injection device according to the second embodiment, whereas a needle shield is in a retracted position.

As illustrated in FIG. 11, the needle shield 1.1 of the second embodiment comprises a retaining catch 1.1.6 that protrudes outwards into a recess formed by the release flap 1.2.7 to retain the needle shield 1.1 in the initial position I, in which the needle shield 1.1 protrudes the support body 1.2 in the retracted position R. Therefore, the recess formed by the release flap 1.2.7 extends over a length of the support body 1.2. The retaining catch 1.1.6 is slidable within the recess formed by the release flap 1.2.7 over a length of the support body 1.2.

Figure 12:
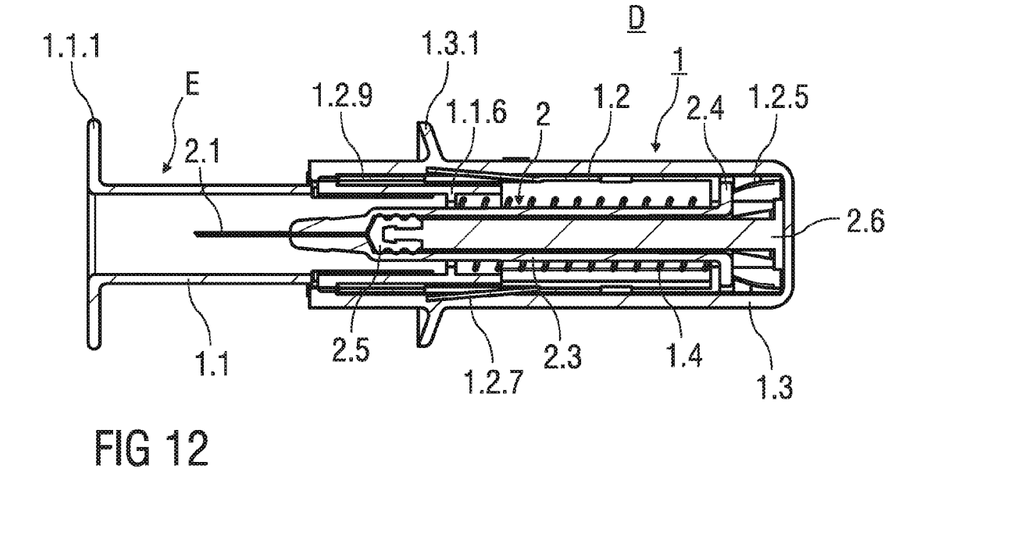
FIG. 12 shows a sectional view of an injection device according to the second embodiment, whereas a needle shield is in an advanced position.

The inwardly protruding dent 1.3.4 engages the release flap 1.2.7 when the support body 1.2 is substantially received within the outer body 1.3 at the end of the injection stroke. The release flap 1.2.7 pivots inwards and presses the retaining catch 1.1.6 in an inward direction to release the retaining catch 1.1.6 from engagement with the recess formed by the release flap 1.2.7. The needle shield 1.1 is moved by the action of the relaxing spring mean 1.4 from the retracted position R to the advanced position E that is shown in FIG. 12.

The needle shield 1.1 locks to the support body 1.2 in the advanced position E, whereas a subsequent proximal movement of the needle shield 1.1 with respect to the support body 1.2 is prevented by the retaining catch 1.1.6 protruding outwards into a distal indent 1.2.9 formed into the distal end of the support body 1.2. A distal movement of the needle shield 1.1 in the advanced position E is prevented by the guide pin 1.1.3 abutting the support body 1.2 in the end position PE, as best seen in FIG. 13.

Figure 13:
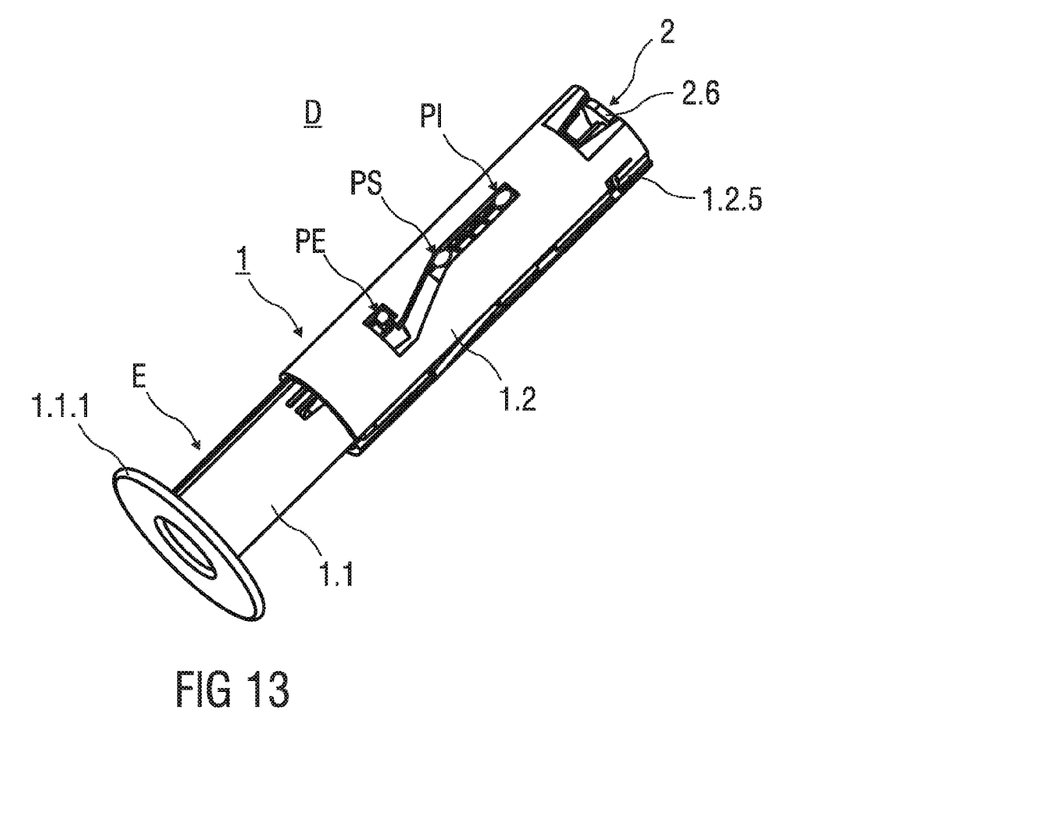
FIG. 13 shows a perspective view of a needle shield and a support body according to the second embodiment, whereas a pre-filled syringe is retained within the support body.

FIG. 13 shows the needle shield 1.1, the support body 1.2 and a pre-filled syringe 2 retained with the support body 1.2 according to the second embodiment of the invention. The needle shield 1.2 is in the advanced position E that corresponds to the end position PE of the guide pin 1.1.3 within the guide track 1.2.2.

Details of the guide track 1.2.2 according to the second embodiment can be seen in FIG. 13. The guide track 1.2.2 of second embodiment does not comprise the flexing gate element 1.2.3 of the first embodiment, as the needle shield 1.2 is retained in the initial position I by an interaction of the retaining catch 1.1.6 and the recess formed by the release flap 1.2.7, as described herein above. The guide track 1.2.2 of the second embodiment is designed as a single continuous track. When the needle shield 1.1 is in the initial position I, the guide pin 1.1.3 is located in the start position PS within the guide track 1.2.2. The guide pin 1.1.3 is located in the intermediate position PI, when the needle shield 1.1 is in the refracted position R.

Figure 14:
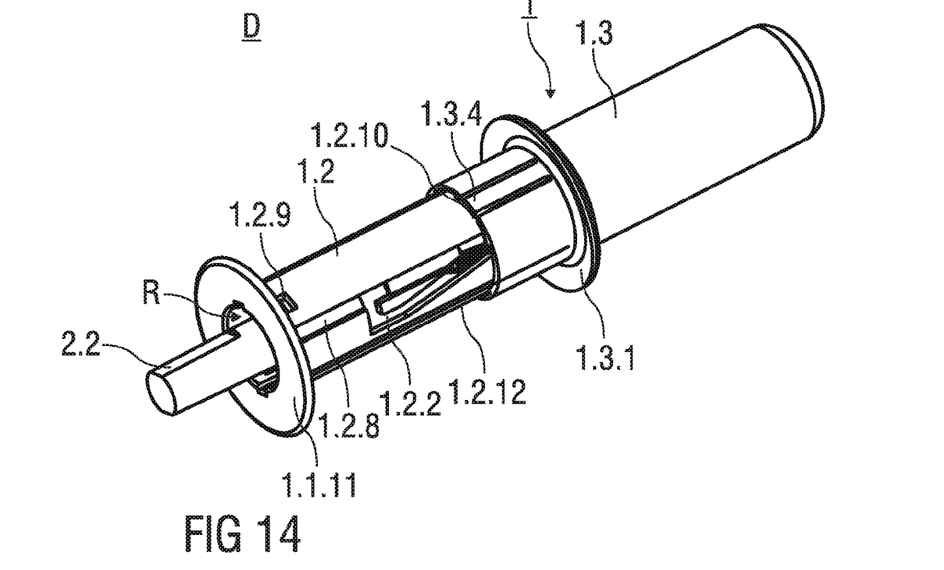
FIG. 14 shows a perspective view of an injection device according to a third embodiment.

FIG. 14 shows a perspective view of the injection device D according to a third embodiment of the invention. Prior to use of the safety device 1 or the injection device D comprising the safety device 1 and the pre-filled syringe 2 received therein, the needle shield 1.1 is in the retracted position R and retained within the support body 1.2. The hypodermic needle 2.1 of the pre-filled syringe 2 is exposed before the injection.

Furthermore, the support body 1.2 of the third embodiment may comprise a skin-contact surface 1.2.11 that is designed to rest on the skin of the patient receiving the injection similar to the skin-contact flange 1.1.1 of the needle shield 1.1 previously described herein before.

An axial tongue 1.2.12 is formed into the outer surface of the support body 1.2. The axial tongue 1.2.12 is received in a correspondingly formed groove when the outer body 1.3 is slid with respect to the support body 1.2 in the distal direction, whereby a relative rotation of the parts 1.2, 1.3 is prevented.

The outer body 1.3 comprises an inwardly protruding dent 1.3.4 that protrudes into a retaining notch 1.2.10 formed into the support body 1.2 to retain the outer body 1.3 relative to the support body 1.2 in a position, in which the support body 1.2 protrudes distally from the distal end of the outer body 1.3. The inwardly protruding dent 1.3.4 is outwardly deflectable when a sufficient force is exerted upon the outer body 1.3 in the distal direction, whereby the inwardly protruding dent 1.3.4 disengages the retaining notch 1.2.10 at the beginning of the injection stroke.

Figure 15:
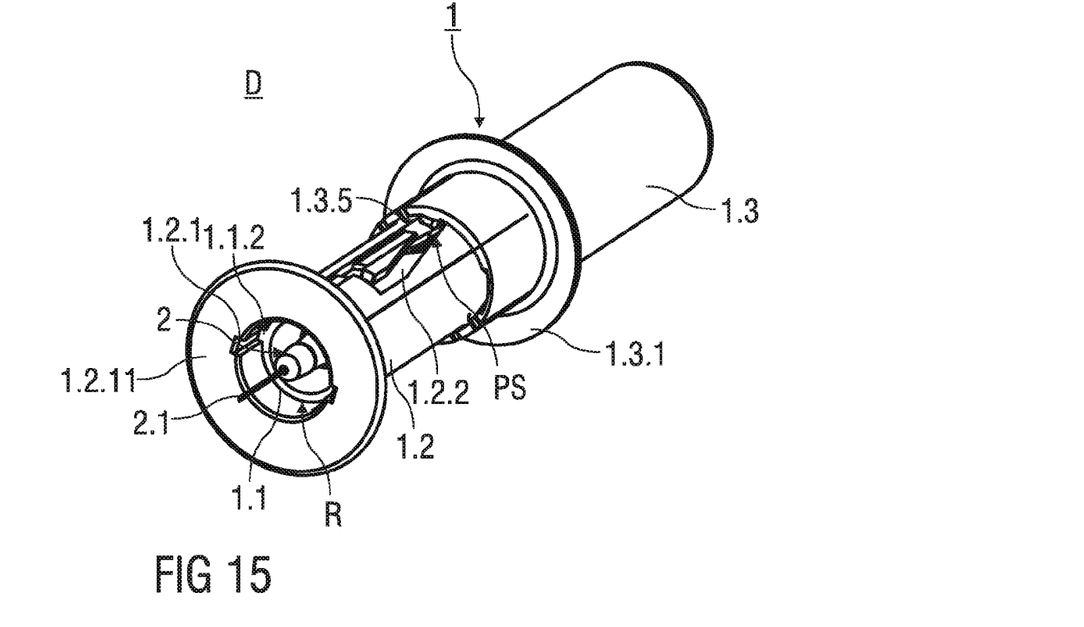
FIG. 15 shows a perspective view of an injection device of the third embodiment, whereby an outer body is retained in a position relative to a support body, so that the support body protrudes the outer body in a distal direction.

As illustrated in FIG. 15, an inward projection 1.3.5 is formed into an inner surface of the outer body 1.3. The inward projection 1.3.5 protrudes inwardly adjacent to the guide track 1.2.2 and abuts the guide pin 1.1.3 to retain the guide pin 1.1.3 in the start position PS, thereby retaining the needle shield 1.1 in the retracted position R. In the third embodiment, the start position PS of the guide pin 1.1.3 is located in proximity of a proximal end of the guide track 1.2.2.

The inward projection 1.3.5 moves within and along a section of the guide track 1.2.2 during the injection stroke, as best seen in FIG. 16A to 16D.

Figures 16A, 16B, 16C, 16D:
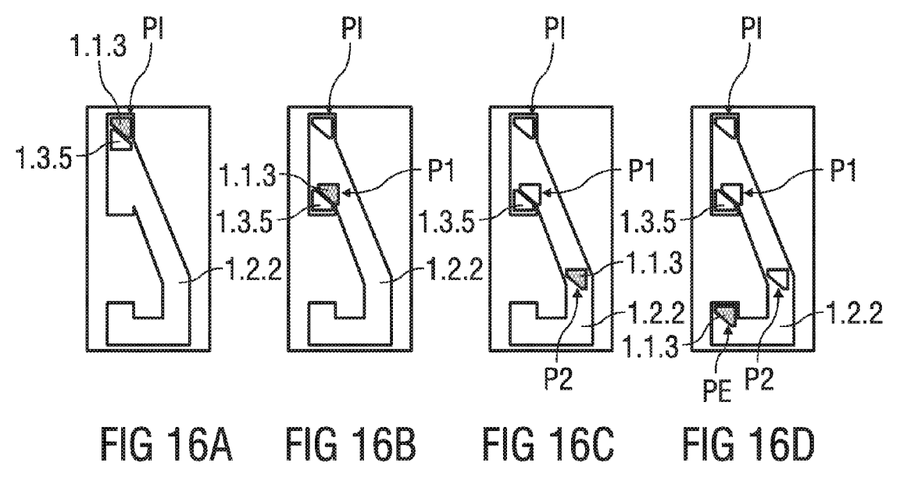
FIGS. 16A to 16D show a guide track formed into a support body and the movement of a guide pin within and along the guide track during an injection according to the third embodiment.

FIG. 16A shows the relative position of the inward projection 1.3.5 and the guide pin 1.1.3 within the guide track 1.2.2 when the needle shield 1.1 is in the refracted position R. The guide pin 1.1.3 is retained in the start position PS by an engagement with the inward projection 1.3.5, so that the needle shield 1.1 is retained in the retracted position R prior to use of the safety device 1.

Both the guide pin 1.1.3 and the inward projection 1.3.5 comprise substantially triangular cross-sections.

After the inwardly protruding dent 1.3.4 disengaged the retaining notch 1.2.10, the inward projection 1.3.5 is free to move along a proximal section of the guide track 1.2.2. The guide pin 1.1.3 follows the distal movement of the inward projection 1.3.5, as the spring mean 1.4 urges the needle shield 1.1 towards the advanced position E.

FIG. 16B shows the position of the inward projection 1.3.5 and the guide pin 1.1.3 at the start of the drug delivery. The triangular shape of the inward projection 1.3.5 urges and redirects the guide pin 1.1.3 laterally into a section of the guide track 1.2.2 that is oriented relative to the central axis A at an acute angle. The safety features of the safety device 1 are activated when the guide pin 1.1.3 reaches the first position P1 shown in FIG. 16B and starts to move further along the guide track 1.2.2 in the distal direction, whereby the guide pin 1.1.3 is urged distally by the spring mean 1.4.

The flexible arm 1.1.4 is laterally deflected when the guide pin 1.1.3 moves along the section oriented at an acute angle relative to the central axis A, whereby the flexible arm 1.1.4 is stressed to bias the guide pin 1.1.3 in a lateral direction.

When the needle shield 1.1 abuts the skin of the patient, the guide pin 1.1.3 stops at a second position P2, as shown in FIG. 16C, and is prevented from moving further distally until the injection device D and/or safety device 1 is taken away from the injection site.

FIG. 16D shows the guide pin 1.1.3 when it reached the end position PE. The guide pin 1.1.3 in the end position PE locks the needle shield 1.1 in the advanced position E. A lateral deflection of the guide pin 1.1.3 is prevented by both the form of the guide track 1.2.2 at the end position PE and by the flexible arm 1.1.4.

Figure 17:
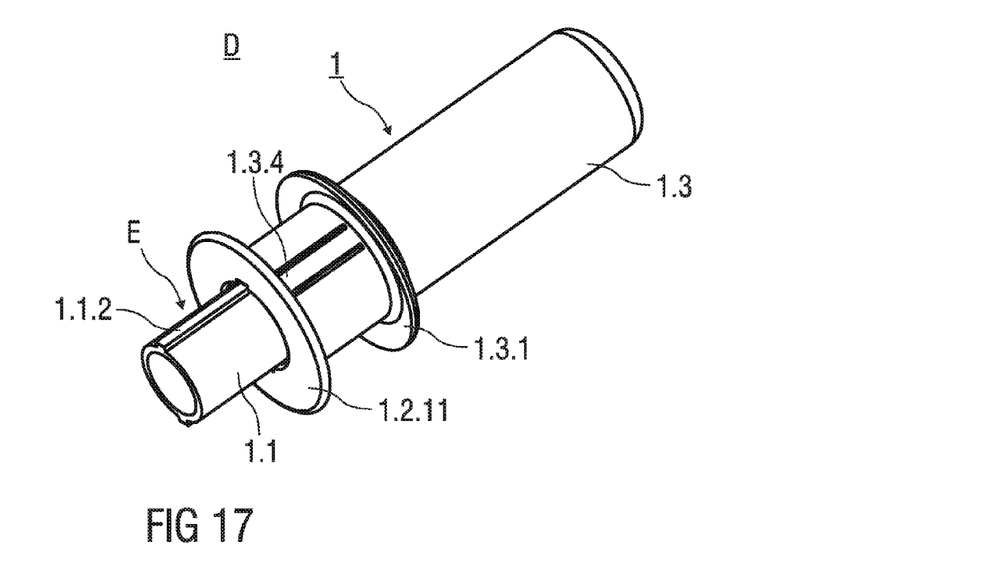
FIG. 17 shows a perspective view of an injection device according to the third embodiment, whereas the needle shield is in an advanced position.

FIG. 17 shows the safety device 1 of the third embodiment, whereas the needle shield 1.1 is locked in the advanced position E. The inwardly protruding dent 1.3.4 protrudes inwardly into the distal indent 1.2.9 to lock the outer body 1.3 with respect to the support body 1.2, whereby a relative movement of outer and support body 1.3, 1.2 is prevented.

FIGS. 18A to 18H illustrate alternative embodiments of the invention. The guide track 1.2.2 is formed into one of the support body 1.2 or the needle shield 1.1 and the flexible arm 1.1.4 is connected to, and in particular integral part of, the other of the support body 1.2 or the needle shield 1.1. Possible different orientations of the guide track 1.2, of the flexible arm 1.1.4 and of the cut-out 1.1.5 that are within the scope of the present invention are also shown. The flexible arm 1.1.4 has a bias to one of the lateral sides of the safety device 1.

Figures 18A, 18B, 18C, 18D:
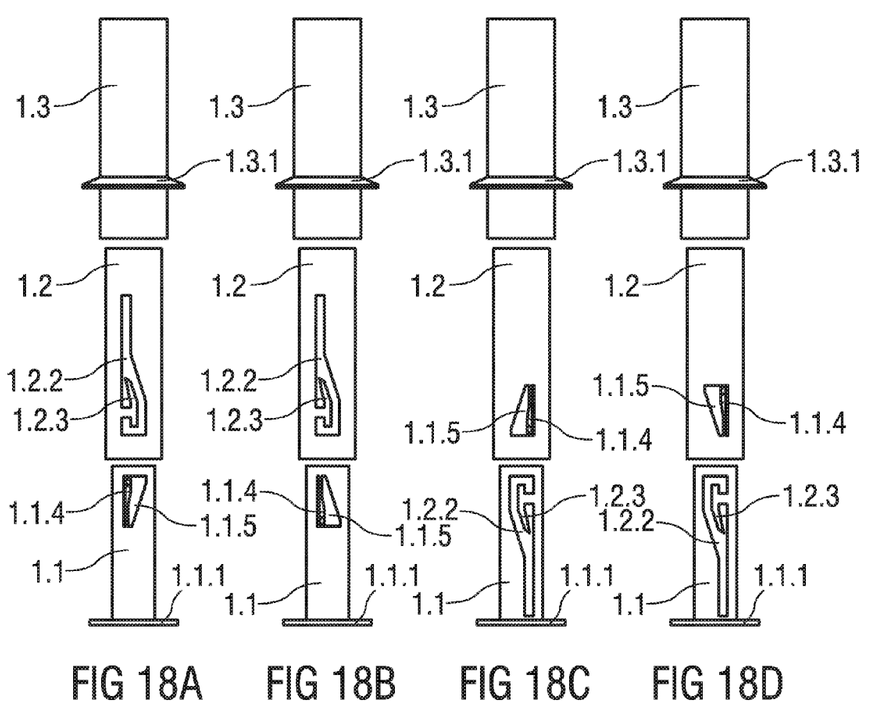
FIG. 18A to 18H show alternative embodiments, whereas a guide track is formed into one of a support body or a needle shield and a flexible arm is connected to, and in particular integral part of, the other of the support body or the needle shield.
Figures 18E, 18F:
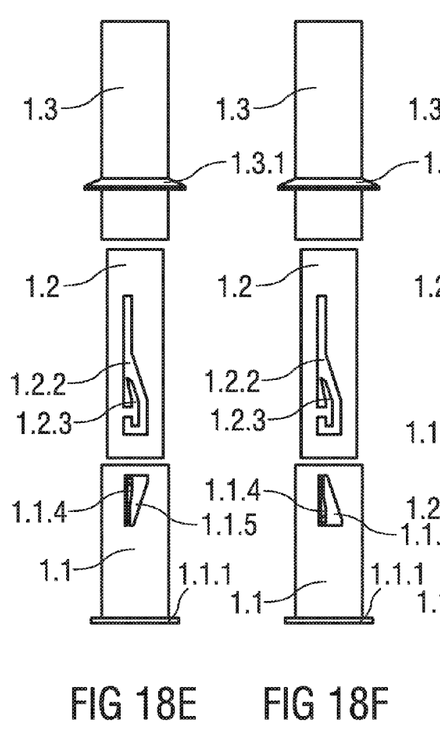
Figures 18G, 18H:
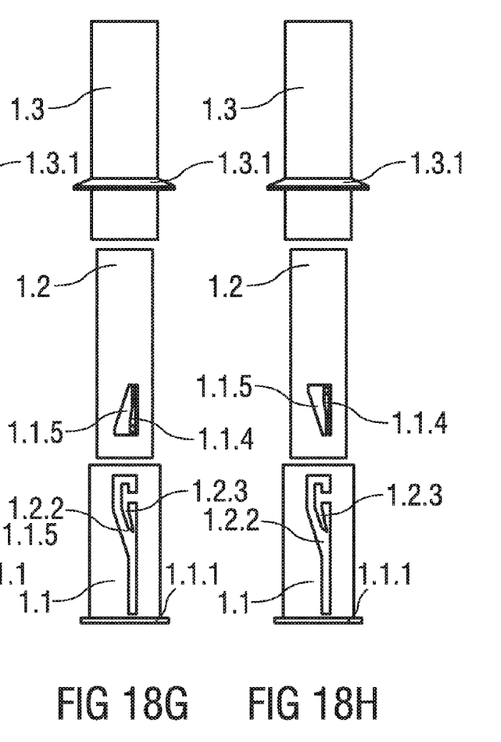

FIG. 18A shows an orientation of the guide track 1.2.2, of the flexible arm 1.1.4 and of the cut-out 1.1.5 according to the first embodiment described herein before.

FIG. 18B shows an alternative embodiment, whereas the flexible arm 1.1.4 extends into the cut-out 1.1.5 from a proximal direction.

FIG. 18C and 18D show other alternative embodiments, in which the guide track 1.2.2 is formed into the needle shield 1.1 and the flexible arm 1.1.4 is connected to the support body 1.2.

FIG. 18E to 18H illustrate alternative embodiments of the invention, wherein the support body 1.2 is received within the needle shield 1.1 when the support body 1.2 and needle shield 1.1 are slid relative to each other.

The invention claimed is:

1. A safety device for a pre-filled syringe, comprising:
an outer body;
a hollow support body to retain the pre-filled syringe therein, wherein the hollow support body is received in the outer body and slidably arranged relative to the outer body to perform an injection stroke;
a hollow needle shield slidable relative to the support body; and
a guiding mechanism to guide the movement of the needle shield relative to the support body, the guiding mechanism comprising
a deflectable flexible arm with a guide pin radially extending therefrom, the flexible arm extending essentially parallel to a central axis of the safety device, and
a guide track configured to guide the guide pin within and along the guide track so that the guide pin follows the guide track when the needle shield is slid relative to the support body,
wherein the flexible arm is configured to be laterally deflected as the guide pin follows the guide track, and
wherein the flexible arm is connected to or is integrally formed to the needle shield or the support body, and the guide track is formed into the other of the needle shield or the support body.

2. The safety device according to claim 1, wherein the guiding mechanism further comprises a longitudinal tongue configured to be received in a longitudinal groove to inhibit relative rotation of the needle shield and the support body when the needle shield is moved with respect to the support body in a distal direction.

3. The safety device according to claim 1, wherein the flexible arm is connected to or is integrally formed to the needle shield and the guide track is formed into the support body.

4. The safety device according to claim 1, wherein the flexible arm is connected to or is integrally formed to the support body and the guide track is formed into the needle shield.

5. The safety device according to claim 1, wherein the flexible arm is deflectable and energizable by the action of a relaxing spring.

6. The safety device according to claim 5, wherein:
the needle shield is arranged to protrude from the support body in an initial position, and
the spring is configured to be in a partially energized state when the needle shield is in the initial position.

7. The safety device according to claim 1, wherein:
the guide pin is arranged to be located in an intermediate position in proximity of a proximal end of the guide track when the needle shield is in a retracted position,
the guide pin arranged to be located in an end position in proximity of a distal end of the guide track when the needle shield is an advanced position, and
the needle shield is arranged to be substantially received in the support body in the retracted position and to protrude from the distal end of the support body in the advanced position.

8. The safety device according to claim 7, wherein the guide pin in a start position, in the end position, and in the intermediate position is non-biased in a lateral direction perpendicular to the central axis.

9. The safety device according to claim 1, wherein the flexible arm is deflectable to bias the guide pin in the lateral direction when the guide pin moves along the guide track from the intermediate position towards the end position.

10. The safety device according claim 1, wherein the needle shield is retainable in an initial position by a flexing gate element configured to retain the guide pin in a start position between a distal end and a proximal end of the guide track.

11. The safety device according to claim 10, wherein the flexing gate element is configured to guide the movement of the guide pin within the guide track.

12. The safety device according to claim 10, wherein the flexing gate element is deflectable in a lateral direction as to allow the guide pin to move from the start position towards the intermediate position.

13. The safety device according to claim 10, wherein a sloped section of the flexing gate element is configured to guide the movement of the guide pin along a section of the guide track and inhibit the guide pin from re-entering the start position.

14. The safety device according to claim 1, wherein:
the needle shield further comprises at least one radial outwardly protruding retaining catch to releasably retain the needle shield in the retracted position, and
the support body further comprises at least one release flap hinged to the support body, wherein an interior surface of the outer body is configured to engage the release flap such that the release flap presses the retaining catch inwardly to release the needle shield.

15. The safety device according to claim 1, wherein the outer body comprises an inward projection to abut the guide pin in an intermediate position to retain the needle shield in a retracted position.

16. The safety device according to claim 15, wherein the guide pin and the inward projection comprise a substantially triangular cross-section.

17. The safety device according to claim 15, wherein the inward projection is movable along a section of the guide track to release the needle shield from being retained in the retracted position.

18. The safety device of claim 1, wherein the outer body is configured to advance a piston rod of a pre-filled syringe in a distal direction when the outer body is translated in the distal direction relative to the support body.

19. The safety device of claim 1, further comprising a longitudinal notch formed into an outer surface of the support body, wherein an inwardly protruding dent is formed into an inner surface of the outer body that is received in the longitudinal notch, the outer body being substantially hollow, and
wherein the flexible arm is configured to be laterally deflected as the guide pin moves along a section of the guide track oriented at an acute angle relative to the central axis.

20. An injection device comprising:
a pre-filled syringe; and
a safety device comprising
an outer body,
a hollow support body to retain the pre-filled syringe therein, wherein the hollow support body is received in the outer body and slidably arranged relative to the outer body to perform an injection stroke,
a hollow needle shield slidable relative to the support body, and
a guiding mechanism to guide the movement of the needle shield relative to the support body, the guiding mechanism comprising
a deflectable flexible arm with a guide pin radially extending therefrom, the flexible arm extending essentially parallel to a central axis of the safety device, and
a guide track configured to guide the guide pin within and along the guide track so that the guide pin follows the guide track when the needle shield is slid relative to the support body;
wherein the flexible arm is configured to be deflected laterally as the guide pin follows the guide track,
wherein the flexible arm is connected to or is integrally formed to the needle shield or the support body, and the guide track is formed into the other of the needle shield or the support body, and
wherein the pre-filled syringe is retained within the support body of the safety device, so that the hypodermic needle protrudes the distal end of the support body, whereas the hypodermic needle is surrounded by the needle shield in the initial position and/or in the advanced position and the hypodermic needle is exposed when the needle shield is in the retracted position.

* * * * *